US009662436B2

(12) United States Patent
Belkin et al.

(10) Patent No.: US 9,662,436 B2
(45) Date of Patent: May 30, 2017

(54) FAIL-SAFE DRUG INFUSION THERAPY SYSTEM

(71) Applicant: ICU Medical, Inc., San Clemente, CA (US)

(72) Inventors: Anatoly S. Belkin, Glenview, IL (US); William K. Day, Hoffman Estates, IL (US); Steve J. Lindo, Chicago, IL (US); James P. Roman, Nashotah, WI (US); Andrei T. Stratan, Mountain View, CA (US)

(73) Assignee: ICU Medical, Inc., San Clemente, CA (US)

( * ) Notice: Subject to any disclaimer, the term of this patent is extended or adjusted under 35 U.S.C. 154(b) by 163 days.

(21) Appl. No.: 14/490,450

(22) Filed: Sep. 18, 2014

(65) Prior Publication Data
US 2015/0088070 A1    Mar. 26, 2015

Related U.S. Application Data

(60) Provisional application No. 61/880,656, filed on Sep. 20, 2013.

(51) Int. Cl.
*A61M 5/142* (2006.01)
*G06F 19/00* (2011.01)

(52) U.S. Cl.
CPC ......... *A61M 5/142* (2013.01); *G06F 19/3418* (2013.01); *G06F 19/3468* (2013.01);
(Continued)

(58) Field of Classification Search
CPC ........ A61M 5/142; A61M 2005/14208; A61M 2205/50; A61M 2205/502;
(Continued)

(56) References Cited

U.S. PATENT DOCUMENTS 4,024,864 A    5/1977   Davies et al.
4,731,051 A    3/1988   Fischell
(Continued)

FOREIGN PATENT DOCUMENTS

EP    2113842 A1    11/2009
WO    0053243 A1    9/2000
(Continued)

OTHER PUBLICATIONS

Graseby Medical Ltd, Model 3000/500 and Micro 3100/505 Volumetric Infusion Pump Technical Service Manual, Apr. 2002, pp. 1-160.
(Continued)

*Primary Examiner* — Kevin C Sirmons
*Assistant Examiner* — Amber Stiles
(74) *Attorney, Agent, or Firm* — Knobbe, Martens, Olson & Bear, LLP

(57) ABSTRACT

A fail-safe drug infusion system, including a user interface controller (UIC) and at least one pump motor controller (PMC), with protocols that enable the PMC to operate therapy delivery for a limited amount of time if the UIC fails or the communication link between the UIC and the PMC is interrupted. Includes synchronization methods to synchronize the delivery information back to the UIC after the UIC reboots or after the communication link is restored. The PMC may apply intelligent fail-safe drug infusion therapy by temporarily displaying therapy information, for example information normally displayed by the UIC, while taking control of alarm signaling and providing minimal user control of the therapy until the UIC restores itself, the infusion completes normally, or the user stops the infusion. If the PMC becomes inoperable, the UIC may wait for the PMC to reboot, or attempt to switch infusion channels to provide robust drug infusion.

17 Claims, 6 Drawing Sheets

(52) U.S. Cl.
CPC ............ *A61M 2005/14208* (2013.01); *A61M 2205/17* (2013.01); *A61M 2205/35* (2013.01); *A61M 2205/50* (2013.01); *A61M 2205/502* (2013.01); *A61M 2205/52* (2013.01)

(58) Field of Classification Search
CPC .......... A61M 2205/52; A61M 2205/17; A61M 2205/35; G06F 19/3468; G06F 19/3418
See application file for complete search history.

(56) References Cited

U.S. PATENT DOCUMENTS

| | | | |
|---|---|---|---|
| 4,854,324 A | | 8/1989 | Hirschman et al. |
| 5,373,454 A | | 12/1994 | Kanda et al. |
| 5,378,231 A | | 1/1995 | Johnson et al. |
| 5,658,131 A | | 8/1997 | Aoki et al. |
| 5,681,285 A | * | 10/1997 | Ford ................ A61M 5/172 604/151 |
| 5,685,844 A | | 11/1997 | Marttila |
| 5,920,054 A | | 7/1999 | Uber, III |
| 6,126,637 A | | 10/2000 | Kriesel et al. |
| 6,257,265 B1 | | 7/2001 | Brunner et al. |
| 6,292,860 B1 | | 9/2001 | Cochcroft, Jr. |
| 6,339,718 B1 | | 1/2002 | Zatezalo et al. |
| 6,427,088 B1 | | 7/2002 | Bowman, IV et al. |
| 6,520,930 B2 | | 2/2003 | Critchlow et al. |
| 6,551,276 B1 | | 4/2003 | Mann et al. |
| 6,554,798 B1 | | 4/2003 | Mann et al. |
| 6,673,033 B1 | | 1/2004 | Sciulli et al. |
| 6,694,191 B2 | | 2/2004 | Starkweather et al. |
| 6,758,810 B2 | | 7/2004 | Lebel et al. |
| 6,811,534 B2 | | 11/2004 | Bowman, IV et al. |
| 6,969,865 B2 | | 11/2005 | Duchon et al. |
| 7,109,878 B2 | | 9/2006 | Mann et al. |
| 7,150,741 B2 | | 12/2006 | Erickson et al. |
| 7,255,683 B2 | | 8/2007 | Vanderveen et al. |
| 7,308,300 B2 | | 12/2007 | Toews et al. |
| 7,524,304 B2 | | 4/2009 | Genosar |
| 7,662,124 B2 | | 2/2010 | Duchon et al. |
| 7,678,071 B2 | | 3/2010 | Lebel et al. |
| 7,776,029 B2 | | 8/2010 | Whitehurst et al. |
| 7,835,927 B2 | | 11/2010 | Schlotterbeck et al. |
| 7,899,546 B2 | | 3/2011 | Sieracki et al. |
| 8,065,161 B2 | | 11/2011 | Assadi et al. |
| 8,066,672 B2 | | 11/2011 | Mandro |
| 8,082,018 B2 | | 12/2011 | Duchon et al. |
| 8,147,448 B2 | | 4/2012 | Sundar et al. |
| 8,206,350 B2 | | 6/2012 | Mann et al. |
| 8,267,892 B2 | | 9/2012 | Spencer et al. |
| 8,579,884 B2 | | 11/2013 | Lanier et al. |
| 2003/0097529 A1 | | 5/2003 | Arimilli et al. |
| 2004/0122530 A1 | | 6/2004 | Hansen |
| 2005/0010269 A1 | | 1/2005 | Lebel et al. |
| 2005/0090808 A1 | | 4/2005 | Malave et al. |
| 2005/0177395 A1 | | 8/2005 | Blomquist |
| 2005/0277911 A1 | | 12/2005 | Stewart et al. |
| 2007/0083870 A1 | | 4/2007 | Kanakogi |
| 2007/0093786 A1 | | 4/2007 | Goldsmith et al. |
| 2008/0147145 A1 | * | 6/2008 | Sieracki ............. A61N 1/37252 607/60 |
| 2008/0256305 A1 | | 10/2008 | Kwon et al. |
| 2009/0005728 A1 | | 1/2009 | Weinert et al. |
| 2009/0275896 A1 | | 11/2009 | Kamen et al. |
| 2009/0326516 A1 | | 12/2009 | Bangera et al. |
| 2010/0160860 A1 | * | 6/2010 | Celentano .......... A61B 5/14532 604/131 |
| 2010/0198196 A1 | | 8/2010 | Wei |
| 2010/0200506 A1 | | 8/2010 | Ware et al. |
| 2010/0204574 A1 | | 8/2010 | Duchon et al. |
| 2010/0292634 A1 | | 11/2010 | Kircher, Jr. |
| 2011/0125095 A1 | | 5/2011 | Lebel et al. |
| 2011/0266221 A1 | | 11/2011 | Ware et al. |
| 2011/0270045 A1 | | 11/2011 | Lebel et al. |
| 2011/0275904 A1 | | 11/2011 | Lebel et al. |
| 2011/0319813 A1 | | 12/2011 | Kamen et al. |
| 2012/0065990 A1 | | 3/2012 | Howard et al. |
| 2012/0066609 A1 | | 3/2012 | Howard et al. |
| 2012/0095437 A1 | | 4/2012 | Hemmerling |
| 2012/0143116 A1 | | 6/2012 | Ware et al. |
| 2012/0150556 A1 | | 6/2012 | Galasso et al. |
| 2012/0179135 A1 | | 7/2012 | Rinehart et al. |
| 2012/0179136 A1 | | 7/2012 | Rinehart et al. |
| 2012/0203177 A1 | | 8/2012 | Lanier |

FOREIGN PATENT DOCUMENTS

| | | |
|---|---|---|
| WO | 2008082854 A1 | 7/2008 |
| WO | 2012048833 A2 | 4/2012 |
| WO | 2012049214 A1 | 4/2012 |
| WO | 2012164556 A1 | 12/2012 |
| WO | 2012170942 A1 | 12/2012 |

OTHER PUBLICATIONS

Cardinal Health Technical Service Manual, Alaris Syringe Pumps, Issue 9, pp. 1-88, Rolle, Switzerland.
Passos, Gesner et al., Distributed Software Platform for Automation and Control of General Anaethesia, pp. 1-8, Lisboa, Portugal.
Graseby Medical Ltd., Illustrated Parts List for Pump Serial No. 3000 to 59,999, Apr. 2002, pp. 1-71.
Micrel Medical Devices Information Sheet, Home Infusion Systems MP Daily +.

* cited by examiner

FIGURE 6
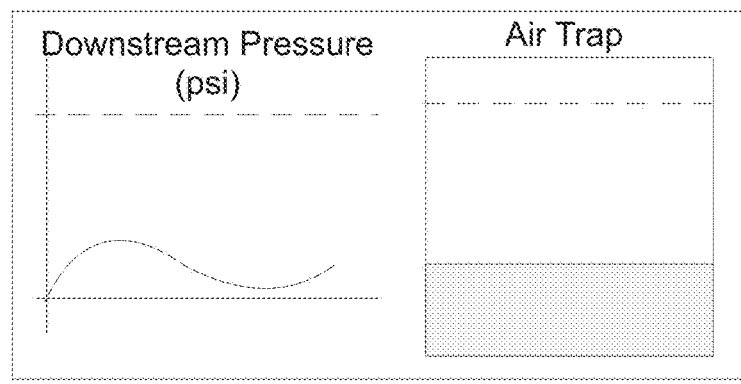

FAIL-SAFE DRUG INFUSION THERAPY SYSTEM

BACKGROUND OF THE INVENTION

Field of the Invention

One or more embodiments of the invention are related to drug infusion therapy systems. More particularly, but not by way of limitation, one or more embodiments of the invention enable a fail-safe drug infusion system, including a user interface controller (UIC) and at least one pump motor controller (PMC), with protocols that enable the PMC to operate therapy delivery for a limited amount of time in the event that UIC fails or the communication link between the UIC and the PMC is interrupted. Embodiments also include synchronization methods to synchronize the delivered drug status back to the UIC after the UIC reboots or after the communication link between the UIC and the PMC is restored. The PMC may apply intelligent fail-safe drug infusion therapy by temporarily displaying therapy information, for example information normally displayed on the UIC, while taking control of alarm signaling and providing minimal user control of the therapy until the UIC restores itself, the infusion completes normally, or the user stops the infusion. If the PMC becomes inoperable, the UIC may wait for the PMC to reboot, or attempt to switch drug infusion channels to provide robust drug infusion.

Description of the Related Art

Generally, current drug infusion systems do not synchronize information between multiple processors, or controllers, in order to enable one processor, or controller, to take over in a fail-safe mode and eventually recover from errors in the other processor or after restoring communications between processors. Some known systems utilize a secondary processor known as a "Safety Processor", wherein such a safety processor may be used to keep the apparatus powered and to ensure delivery of a drug. These locally redundant systems generally switch to a redundant processor that may contain complex business logic inherent in the first processor, i.e., in the user interface code, which limits the robustness of the system since an error on the first processor may also occur on a second processor having the same or similar complex software code. In the event of a fault detected by either processor, including failure or loss of communication with the primary processor, the infusion may be stopped. Absent prompt caregiver attention and intervention, stopping some drug infusions may result in a delay in therapy that could lead to serious injury to a patient or even death.

In addition, current distributed systems appear to lack any suggestion of using a user interface controller (UIC), and a pump motor controller (PMC), that both maintain redundant, yet separate ability to manage alarm signals, user inputs, user displays, etc., to ensure continuous delivery of drugs in a robust manner. For example, typical systems lack any disclosure of limited backup capability in a microcontroller in the PMC, for example do not display infusion status on the PMC display that would normally be displayed on the UIC. Hence, these systems cannot possibly maintain fail-safe operation since no backup functionality exists for displaying infusion status, alarms or signals.

For example, U.S. Pat. No. 7,835,927 to Coffman et al., entitled "Medication Management System", discloses a medical database carrier that may communicate information regarding medication delivery and other patient information between a control system in communication with a care-giving facility. As such, the system appears to lack any disclosure of fail-safe operation if a communication link between a first processor and a second processor is lost. For example, the system does not contemplate replacing the second processor's duties for the current delivery process, to continue to deliver a drug or medication, and to continue to power the system. The system also lacks any disclosure or suggestion of synchronizing delivery status after the communication link has been restored.

U.S. Patent Publication 20100200506 to Boehnlein et al., entitled "Flow Balancing and Synchronization System and Method, Especially for Citrate", appears to disclose a renal failure therapy system including a blood pump, a citrate pump and a control unit configured to automatically control the blood pump and the citrate pump, for synchronization of flow rates. The system of Boehnlein et al., for example, discloses automatically adjusting for variations in flow rate, if one pump increases or decreases flow rate, using an external pump. In addition, the system appears to disclose a control processor in communication with a safety processor and two pumps, to monitor error conditions, receive status and parameter information from each of the pumps, ensuring safety limits are met. For example, if one pump is only inputting less ml/hour, an alarm is generated and the system automatically compensates for the loss by varying the pump rate of another pump. However, it appears as though the system lacks any disclosure of fail-safe operation if a communication link between a first processor and a second processor is lost. For example, the system does not contemplate replacing the second processor's duties for the current delivery process, to continue to deliver a drug or medication, and to continue to power the system. The system also lacks any disclosure or suggestion of synchronizing delivery statuses after the communication link has been restored.

In summary, there are no known fail-safe drug infusion therapy systems, including a first processor and a second processor, with protocols that enable the second processor to operate therapy delivery for a limited amount of time in the event that the communication link between the first processor and the second processor is interrupted that include synchronization methods to synchronize the second processor and the delivered drug status back to the first processor. In addition, there are no known fail-safe drug infusion therapy systems that display infusion progress and infusion statuses for example on a limited display connected to the PMC when the UIC is inoperable or when communication link is interrupted. For at least the limitations described above there is a need for a drug infusion system for synchronized fail-safe drug infusion therapy.

BRIEF SUMMARY OF THE INVENTION

One or more embodiments described in the specification are related to drug infusion therapy systems that provide synchronized fail-safe drug infusion therapy. In one or more embodiments, the drug infusion system includes distributed components that include a user interface controller (UIC) generally having complex business logic and complex user interface functionality, and at least one pump motor controller (PMC) acting as a real-time controller, wherein the UIC and PMC communicate over a communication link.

According to at least one embodiment, the UIC includes a first processor, a first memory coupled with the first processor and a user interface display coupled with the first processor. In at least one embodiment, the PMC includes a second processor, a second memory coupled with the second processor and a pump motor controller display coupled with the second processor. The second processor, in at least one embodiment, controls a pump motor to deliver a fluid, for example one or more drugs. The pump motor controller display may have limited capabilities and be utilized as a backup display if the UIC cannot display infusion status. In one or more embodiments, the first processor and the second processor are communicatively synchronized via the communication link.

Embodiments of the invention may be also redundant on a local component level as well. For example, in one or more embodiments, the UIC can "move" a running infusion to another unused channel. For example, in a dual channel system configuration, if one channel fails while executing a program, the UIC can prompt the user to move the administration set, which may include a cassette, over to the other channel and resume the infusion from there. Thus embodiments, of the invention may include robust distributed and local components.

By way of one or more embodiments, the UIC may build a "token" that contains the drug infusion program as confirmed by the user along with the current infusion status. Specifically, the "token" or drug infusion program may include all program steps, all infusion related options and current status, which is initially null before infusion begins in one or more embodiments. The token may act in one or more embodiments as a semaphore for the component that has the responsibility to maintain the current infusion status for example.

The UIC may pass the token to the PMC to initiate drug infusion. The PMC then runs the infusion therapy and monitors communication with the UIC. While running the program, the PMC updates the UIC with an infusion status update message. The message may contain the currently executing program and associated program steps, the infusion related options and current status, e.g., the most up to date information about the delivered and remaining to be delivered infusion parameters. Under normal processing, the status details are synchronized with the UIC over time, for example at predefined time intervals.

If the UIC fails, for example via failure to provide heartbeat to the PMC, the PMC takes control of the alarm components and signals the failure to the user, albeit on a limited display local to the PMC for example or alternatively using operable portions of the UIC related display. During this time, the PMC may display infusion progress and status locally, for example replacing the current limited text or graphics display with infusion related information that would normally be displayed on the UIC. Alternatively, if any components normally controlled by the UIC, such as the display are still operative, then the PMC may pass the information to the display of the UIC or a display common to both the UIC and PMC. The PMC may also raise audio and visual alarms locally or remotely until the UIC is functional, which is generally the responsibility of the UIC when functional. In one or more embodiments, the display or backup display of the PMC may show the amount of time that the PMC may operate independently based on the current drug infusion program for example. When another infusion related event occurs, such as an occlusion, or air-in-line, etc., the PMC takes intelligent local actions based on the initial program received to handle the condition, for example stop or not stop infusion accordingly along with signaling of the new alarm condition. When any of the alarm conditions are cleared, including if the UIC recovers and reestablishes communication with the PMC, the system uses normal alarm condition clearing protocols.

If the PMC fails, for example via failure to provide heartbeat to the UIC, then the UIC may assert control of the token with the last known infusion parameters until the PMC reboots. The UIC may then pass the token back to the PMC with the last known infusion related information.

In one or more embodiments, each of the first memory of the first processor and the second memory of the second processor may include any type of redundant drug infusion data structures, for example queues, lists, databases or any other type of data structure. Queues such as service queues may be utilized to store delivery requests and queues such as redundant drug infusion working queues may be utilized to store in-progress infusion requests respectively. Any other data structures or techniques may be utilized to ensure synchronization of drug infusion information in keeping with the scope of the invention.

BRIEF DESCRIPTION OF THE DRAWINGS

The above and other aspects, features and advantages of the invention will be more apparent from the following more particular description thereof, presented in conjunction with the following drawings wherein:

FIG. 6 shows exemplary pump motor controller associated displays under normal operation and under UIC failure wherein the PMC processor, e.g., second processor, is further configured to display a limited version of infusion information on the optional secondary user interface display that is normally displayed by said first processor on the first user interface display.

DETAILED DESCRIPTION OF THE INVENTION

A fail-safe drug infusion system will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
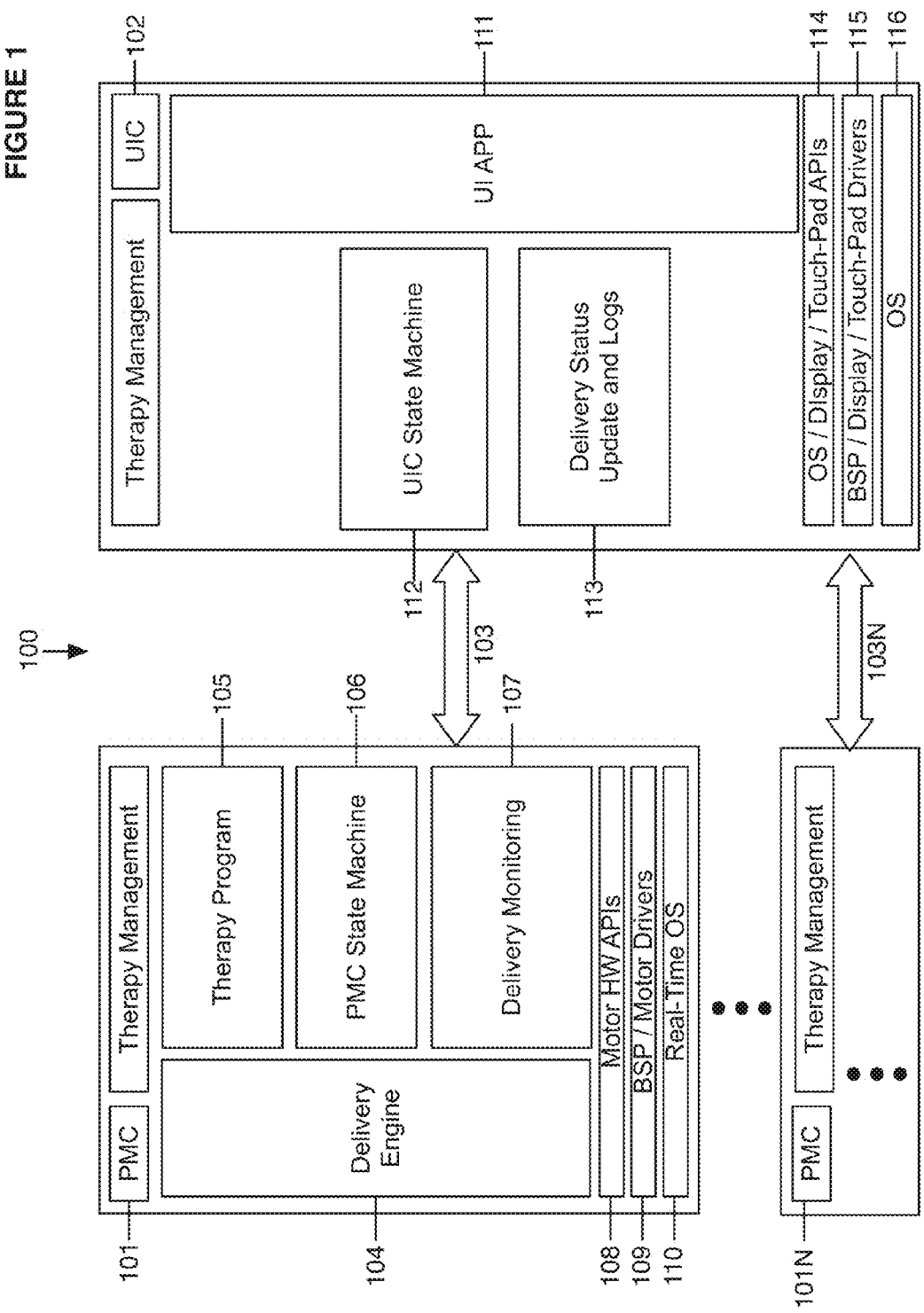
FIG. 1 shows a logical diagram of the fail-safe drug infusion therapy system according to one or more embodiments of the invention.

FIG. 1 shows a schematic overall diagram of the fail-safe drug infusion therapy system according to one or more embodiments of the invention. As shown in FIG. 1, by way of one or more embodiments, each of the first memory, that holds user interface app 111, user interface controller state machine 112, delivery status update and logs 113, operating system, display and touch-pad APIs 114, board support package, display and touch-pad drivers 115 and operating system 116 of the first processor 102 and the second memory, that holds delivery engine 104, therapy program 105, PMC state machine 106, delivery monitoring information 107, motor hardware APIs 108, board support package, motor drivers 109 and real-time operating system 110 of the second processor 101 include redundant drug infusion related information and status. The redundant drug infusion related information may be stored in the delivery monitoring 107 and delivery status 113 memory areas for example or in any other portion of memory in either the PMC or UIC. In one or more embodiments UIC 102 may control more than one PMC, e.g., PMC 101 and 101N.

In at least one or more embodiments of the invention, when the communication link is initially established between the first processor and the second processor, the first processor in the PMC obtains an infusion program and is initially responsible for maintaining infusion related information. In one or more embodiments this is accomplished with a "token" that contains the drug infusion program as confirmed by the user along with the current infusion status. Specifically, the "token" or drug infusion program may include all program steps, all infusion related options and current status, which is initially null before infusion begins in one or more embodiments. The token may act in one or more embodiments as a semaphore for the component that has the responsibility to maintain the current infusion status for example. According to at least one embodiment, the first processor may send a first delivery request from the first processor drug infusion service queue to the first processor drug infusion working queue. When the first delivery request is in the first processor drug infusion working queue, the first processor, when in active mode, may send a delivery request notification to the second processor via a first delivery request identification code. Any other type of data structure, messages or communication protocols that enable the PMC and UIC to maintain and synchronize infusion data after either processor malfunctions and/or enable the PMC to display infusion related information that is normally displayed on the UIC if the UIC malfunctions is in keeping with the scope of the invention.

In at least one or more embodiments, when the second processor receives the delivery request identification code, the second processor may transfer the first delivery request from the second processor drug infusion service queue to the second processor drug infusion working queue, and may command the pump motor to deliver the fluid. According to at least one embodiment of the invention, if the first processor fails or if the communication link between the first processor and the second processor is interrupted, the second processor may apply fail-safe therapy and shift from the slave mode to the master mode in order to process the second processor drug infusion service queue and drug infusion working queue to command the pump motor to deliver the fluid.

By way of one or more embodiments of the invention, when the pump motor delivers the fluid, the second processor creates a status report with status report information, such that the second processor may send the status report information to the first processor. In at least one embodiment, the first processor receives the status report information from the second processor and updates a fluid delivery status display on the user interface display 202 (see FIG. 2). According to one or more embodiments of the invention, the information includes the activated delivery requests, the activated fluid deliveries, completed delivery requests, completed fluid deliveries, and an ordered list of the delivery requests remaining in the first processor drug infusion service queue.

In one or more embodiments of the invention, the first processor may send a first delivery suspend request to the second processor in order to suspend the first delivery request, such as when the user initiates a first delivery suspend command, when the first processor detects an error, when the second processor detects an error, or any combination thereof. According to at least one embodiment, the second processor may receive the first delivery suspend request, stop the pump motor delivery of the fluid prior to completion of the delivery of the fluid such that undelivered fluid volume remains, and suspend the first delivery request in the second processor drug infusion working queue.

In at least one or more embodiments of the invention, the error detected by the first processor and/or the error detected by the second processor may include one or more of a UIC 102 failure, wherein infusion is continued while the UIC 102 reboots, motor encoder position error, wherein the motor encoder may attempt to recalibrate itself and pumping is continued instead of alarming and/or stopping infusion, low battery capacity, low battery voltage, indication of a lack of an installed battery, high battery charging current, a stuck button wherein the button is not the emergency stop button 201, a buzzer and/or speaker failure during infusion, a drug library download failure, wherein the UIC 102 may include or may access a drug library and during such a failure the UIC 102 may revert back to a previously installed drug library PIDL or a default drug library DDL. In one or more embodiments, the errors may include failure of the UIC 102 to write to log, a volume overshoot, lost communication with one or more external drug libraries, high ambient temperature or temperature sensor failure, and no heartbeat and/or communications between the UIC 102 and the PMC 101.

In one or more embodiments of the invention, the first processor may send a second delivery request from the first processor service queue to the first processor drug infusion working queue. As such, in at least one embodiment, when the second delivery request is in the first processor drug infusion working queue, the first processor may send a second delivery request notification to the second processor via a second delivery request identification code, and when the second processor receives the second delivery request identification code, the second processor may transfer the second delivery request from the second processor service queue to the second processor drug infusion working queue, such that the pump motor delivers the fluid.

In at least one embodiment of the invention, for piggyback requests for example, when the second delivery request fluid delivery is completed, the second processor may update the fluid delivery status display, and the first processor may send the suspended first delivery request to the second processor such that the pump motor delivers the remaining undelivered fluid volume.

By way of one or more embodiments, if the communication link 103, or 103N when communicating with more than one PMCs, between the first processor and the second processor is interrupted during fluid delivery of the second delivery request, upon completion of the second delivery request, the second processor may locate the suspended first delivery request from the second processor service queue and may transfer the suspended first delivery request to the second processor drug infusion working queue in order to deliver the remaining undelivered fluid volume. In at least one embodiment of the invention, when the remaining undelivered fluid volume is delivered, the first processor may locate a next delivery request from the delivery requests in the first processor service queue, such that the pump motor delivers the fluid. In one or more embodiments, when the remaining undelivered fluid volume is delivered, the second processor may locate a next delivery request from the delivery requests in the second processor service queue, such that the pump motor delivers the fluid.

In at least one embodiment, when the communication link 103 between the first processor and the second processor is interrupted, the second processor may provide therapy for a predefined time in active mode, or display information on the pump motor controller display or any combination thereof. The information may include the activated delivery requests, the activated fluid deliveries, completed delivery requests, completed fluid deliveries, and an ordered list of the delivery requests remaining in said second processor service queue.

According to at least one embodiment of the invention, if the communication link 103 between the first processor and the second processor is reestablished, the second processor may enter a recovery synchronization mode while remaining in the active mode, such that the second processor may send status report information to the first processor. The status report information may include one or more of the activated delivery requests, the activated fluid deliveries, completed delivery requests, and completed fluid deliveries. In embodiments that employ a token or semaphore, the PMC may be considered to control the semaphore if the communication link 103, or again 103N for multi-PMC embodiments, is unavailable. In this manner, when the link is reconnected or otherwise restored, the PMC may deliver updated infusion status to the UIC and retain the token.

By way of one or more embodiments of the invention, the user interface application 111 may include indicators, status icons and alarms, as well as one or more buttons such as a power on/off button, a stop button, a silence or mute button, a clean lock button, a load/eject button and any type of information button. In one or more embodiments, the user interface application 111 may include therapy entry and alteration options, such that the therapy entry options may include one or more of basic, concurrent delivery from the two or more channels, bolus, multistep, intermittent infusions and interchannel sequencing therapy delivery. In addition, in one or more embodiments, the alteration options may include one or more of titrating, delay start, piggyback delivery (for example using a second channel then a first channel), bolus and priming options. As such, the system may recover from one or more errors with zero delay in therapy. In at least one embodiment, the alarms may include one or more of a visual alarm and an audio alarm, such that when the communication link between the first processor and said second processor is interrupted, the pump motor controller (PMC) 101 may provide one or more of the visual alarm and the audio alarm on the pump motor controller display. In one or more embodiments, when the communication link 103 between the first processor and the second processor is interrupted, the second processor may display a duration of how long the second processor is able to operate independently of the first processor on the pump motor controller display. In one or more embodiments, the duration may be displayed as a countdown of a time remaining that the second processor is able to operate independently of the first processor on the pump motor controller display.

In one or more embodiments recoverable error conditions such as upstream or downstream occlusions or air related events or motor encoder position error, battery, button, speaker, backlight, drug library download failure, log failure, volume overshoot, temperature or other errors may be displayed by the UIC or PMC for example as alarms in a local or remote manner. Power-on diagnostics for the PMC may test administration sets or cassettes and in case of administration set or cassette error, prompt the user to change administration sets or cassettes and inform the user that the current channel requires service for example. Active run-time diagnostics for the PMC that indicate that the UIC is inoperative and may switch the PMC display information from occlusion pressure, air monitor, etc., related information to an infusion status view that shows information normally displayed on the UIC, albeit in an abbreviated or limited text or graphics based fashion to the extent possible on the limited PMC display. When the UIC recovers or the communication link 103 is available, the PMC will generally then switch back to its normal occlusion, air, etc., display, and update the UIC with current infusion status and continue to execute the therapy program in progress. The UIC will attempt to reboot if a malfunction occurs and request the synchronization data after reboot and power-on diagnostics for example.

Figure 2:
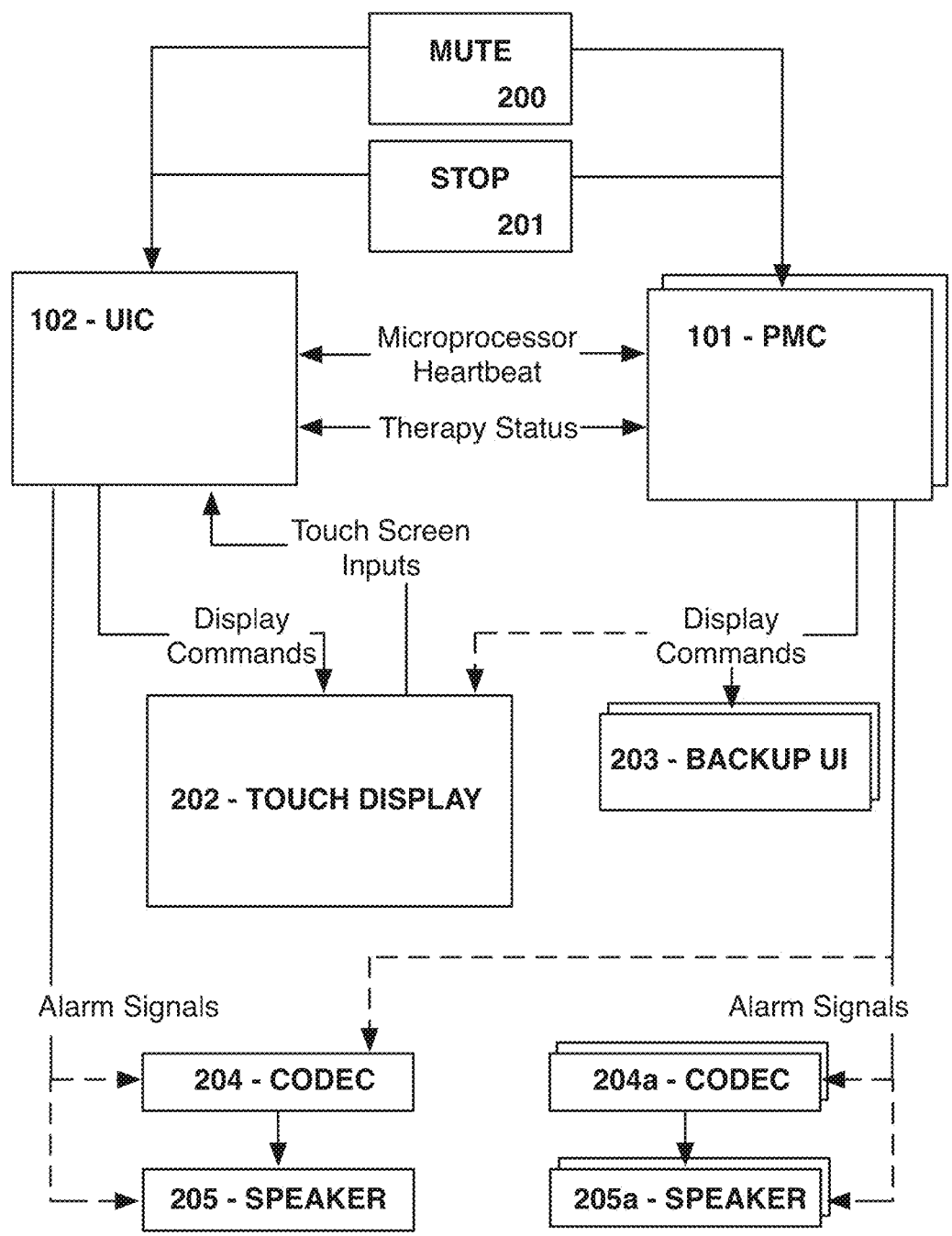
FIG. 2 shows a simplified hardware architectural diagram of the fail-safe drug infusion therapy system according to one or more embodiments of the invention.

FIG. 2 shows an architectural diagram of the fail-safe drug infusion therapy system according to one or more embodiments of the invention. As shown in FIG. 2, the fail-safe drug infusion therapy system may include an emergency stop button 201, a silence or mute button 200, a touch display 202, a backup user interface 203, for example to display infusion related information via the PMC when the UIC is unavailable, a codec 204 and a speaker 205 in communication with the codec 204. More than one PMC may be utilized in the system as depicted by another PMC block shown behind PMC 101. Alternatively, or in combination, the PMC may include multiple backup user interfaces, or they may be associated with respective PMCs. The multiple backup UIs are shown as stacked blocks behind backup UI 203. Embodiments may also include multiple codecs and speakers 204a and 205a respectively that are available for use by one or more PMCs. In at least one embodiment of the invention, while the PMC 101 is running and the UIC 102 is unavailable, inoperative or down, the PMC 101 may display rudimentary status messages on backup user interface display 203 or alternatively if a separate communication link exists, on the touch display 202. In one or more embodiments, the optional codec 204 and the speaker 205 may be in direct or indirect communication. The emergency stop button 201 is in communication with the UIC 102 and the PMC 101. As also shown in FIG. 2, the PMC 101 and the UIC 102 may communicate in a bidirectional manner to deliver a microprocessor heartbeat and a therapy status. In at least one embodiment, the UIC 102 may communicate bidirectionally with the touch display 202 in order to deliver display commands from the UIC 102 to the touch display 202, and send touch screen inputs from the touch display 202 to the UIC 102. In one or more embodiments, the PMC 101 may deliver display commands to the backup user interface 203 or optionally to the touch display 202 if an appropriate communication link exists therebetween. In at least one embodiment of the invention, both the PMC 101 and the UIC 102 may delivery alarm signals to the codec 204. In another embodiment of the invention, PMC 101 may delivery alarm signals to a backup speaker 205a or optionally via codec 204a.

By way of one or more embodiments of the invention, if the PMC 101 fails or loses communication with the UIC 102, the UIC 102 may use a redundant set of therapy status information to continue therapy delivery, for example via a different operational PMC channel, wherein the redundant set of therapy status information is updated periodically from the PMC 101. As such, the UIC 102 may hold the current therapy status, wait for the PMC 101 to reboot (if needed) and pass operator (user) intervention. In one or more embodiments, the PMC 101 may perform recovery synchronization and deliver the current status and history log information to the UIC 102, ensuring there is no interruption in therapy history in the log files and automated self-recovery.

Figure 3:
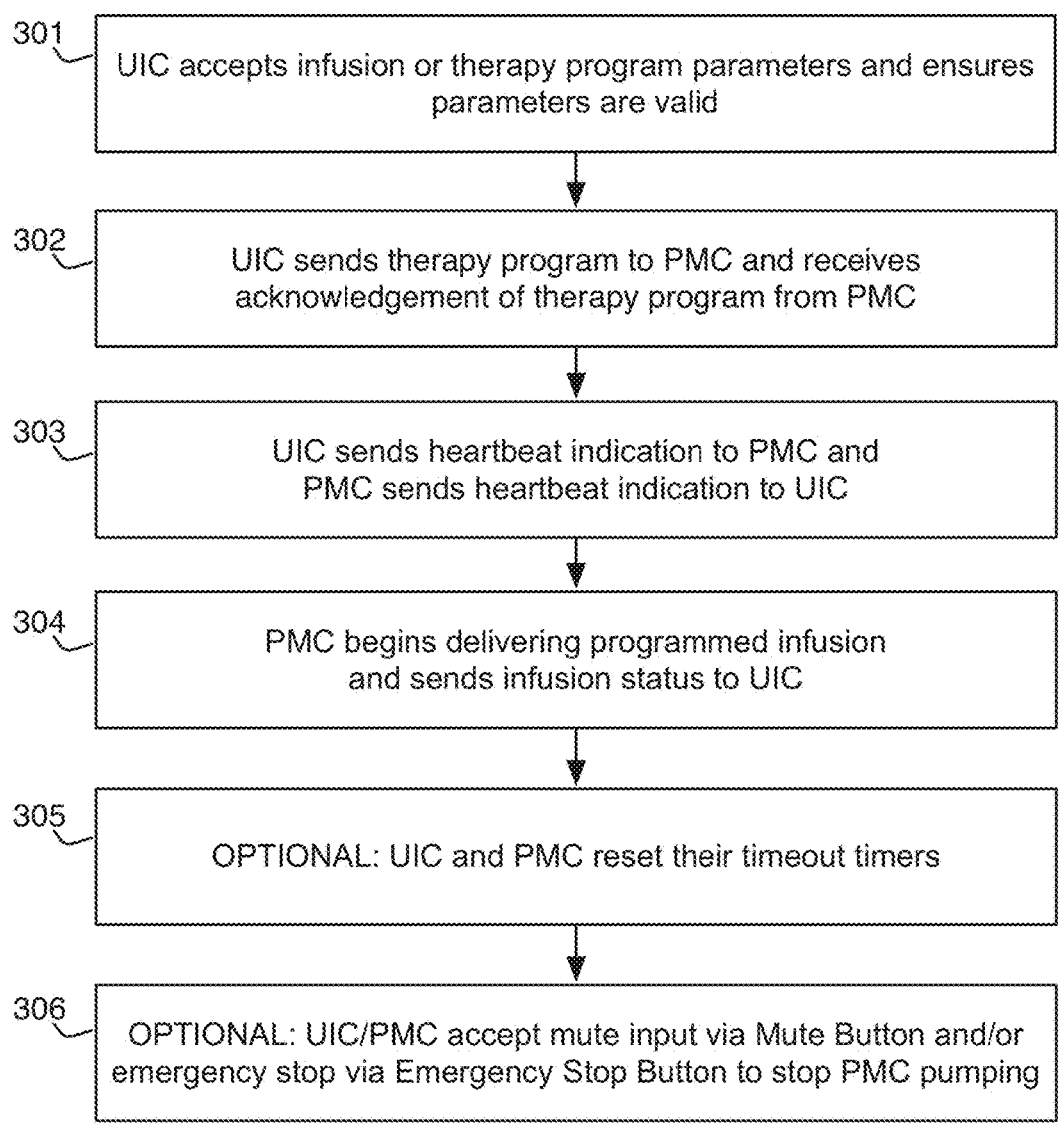
FIG. 3 shows a communications flowchart between the user interface controller and pump motor controller during infusion, according to one or more embodiments of the invention.

FIG. 3 shows a communications flowchart between the user interface controller and pump motor controller during infusion, according to one or more embodiments of the invention. As shown in FIG. 3, under normal operation where both the PMC and UIC are functioning and communicative at 301, the UIC 102 may accept infusion or therapy parameters manually from a user or electronically from another computer system within a hospital (not shown for brevity), and ensure the parameters are valid. In at least one embodiment, at 302 the UIC 102 may send a therapy program to the PMC 101 and receive acknowledgement of the therapy program from the PMC 101. UIC 102 may send a heartbeat indication at 303 to the PMC 101 and a heartbeat indication may be sent from the PMC 101 to the UIC 102. In one or more embodiments, at step 304, the PMC 101 may begin delivering a programmed infusion, or this may occur at any other time after the infusion program is received by the PMC, and the PMC send an infusion status to the UIC 102, wherein the UIC 102 may acknowledge receipt of the infusion status. At step 305, the timeout timers in the UIC and PMC may be optionally reset in software in one or more embodiments, otherwise, timers may be automatically reset if implemented in hardware for example, and the UIC 102 may update status logs. In at least one or more embodiments of the invention, optional step 306 may include accepting a mute input via the Mute Button 200 and/or an emergency stop signal using the emergency stop button 201, for example as accepted by the system from a user, to stop the PMC 101 from pumping. In one or more embodiments, when the emergency stop button 201 is used, the emergency stop signal is simultaneously sent to the UIC 102.

Figure 4:
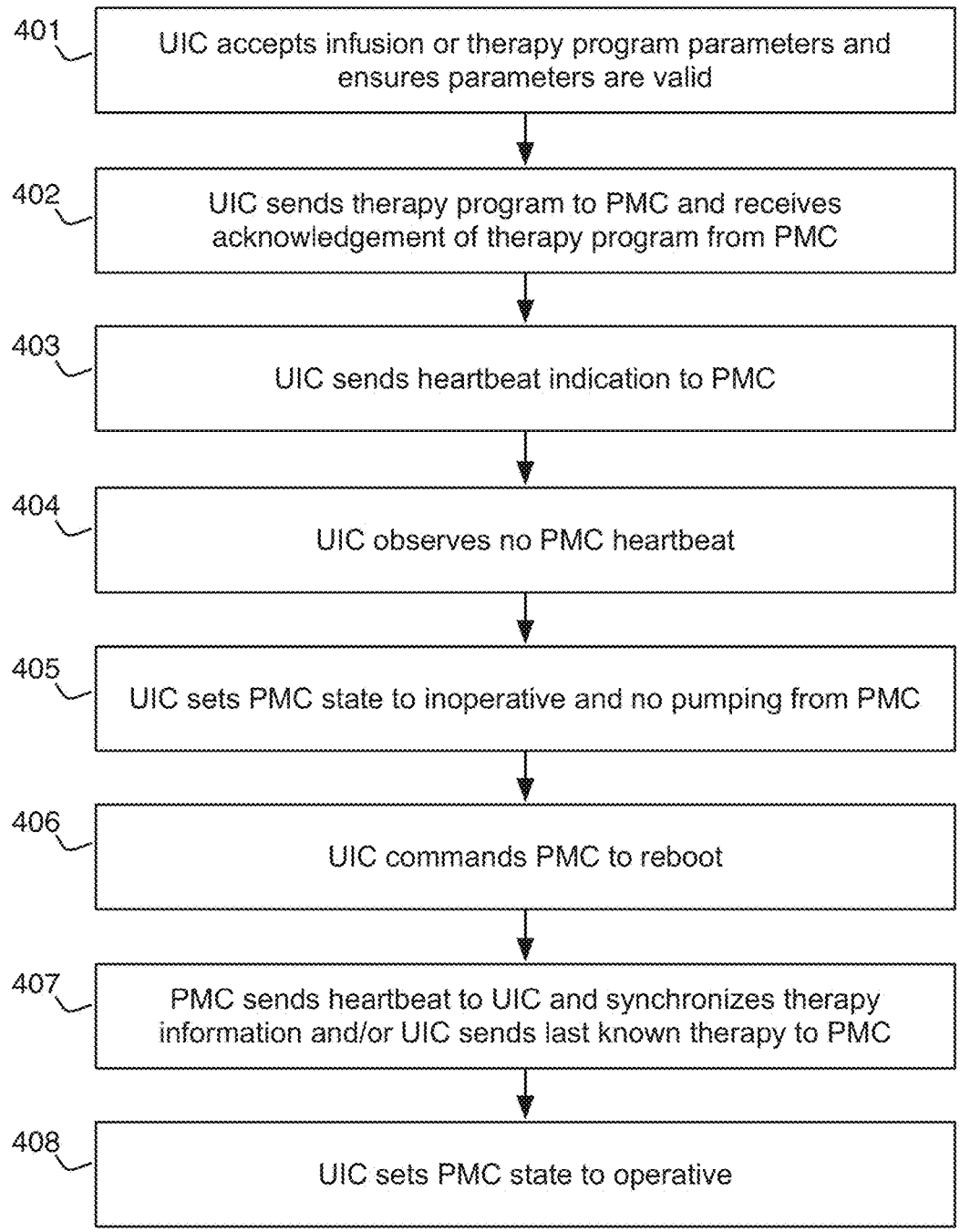
FIG. 4 shows a flowchart illustrating a response to the pump motor controller malfunctioning during infusion, according to one or more embodiments of the invention.

FIG. 4 shows a flowchart illustrating a response due to a pump motor controller malfunction during infusion, according to one or more embodiments of the invention. As shown in FIG. 4, at step 401, the UIC 102 may accept infusion or therapy parameters manually from a user or electronically from another computer system within a hospital (not shown for brevity), and ensure the parameters are valid. In at least one embodiment, at 402 the UIC 102 may send a therapy program to the PMC 101 and receive acknowledgement of the therapy program from the PMC 101. UIC 102 may send a heartbeat indication to the PMC 101 at 403. In one or more embodiments of the invention, the UIC 102 may not receive or otherwise observe a PMC heartbeat at 404, and may then set a PMC state to inoperative at 405, wherein pumping generally does not occur while the PMC 101 is inoperative. At 406, the UIC 102 may command the PMC 101 to reboot, such that the PMC 101 reboots, and at step 407, the PMC 101 then delivers a heartbeat indication to the UIC 102, and the UIC 102 sends a last known therapy to the PMC 101. In one or more embodiments, the PMC 101 may deliver an acknowledgement receipt to the UIC 102 of the last known therapy data, in which at step 408, the UIC 102 may set the PMC state to operative.

Figure 5:
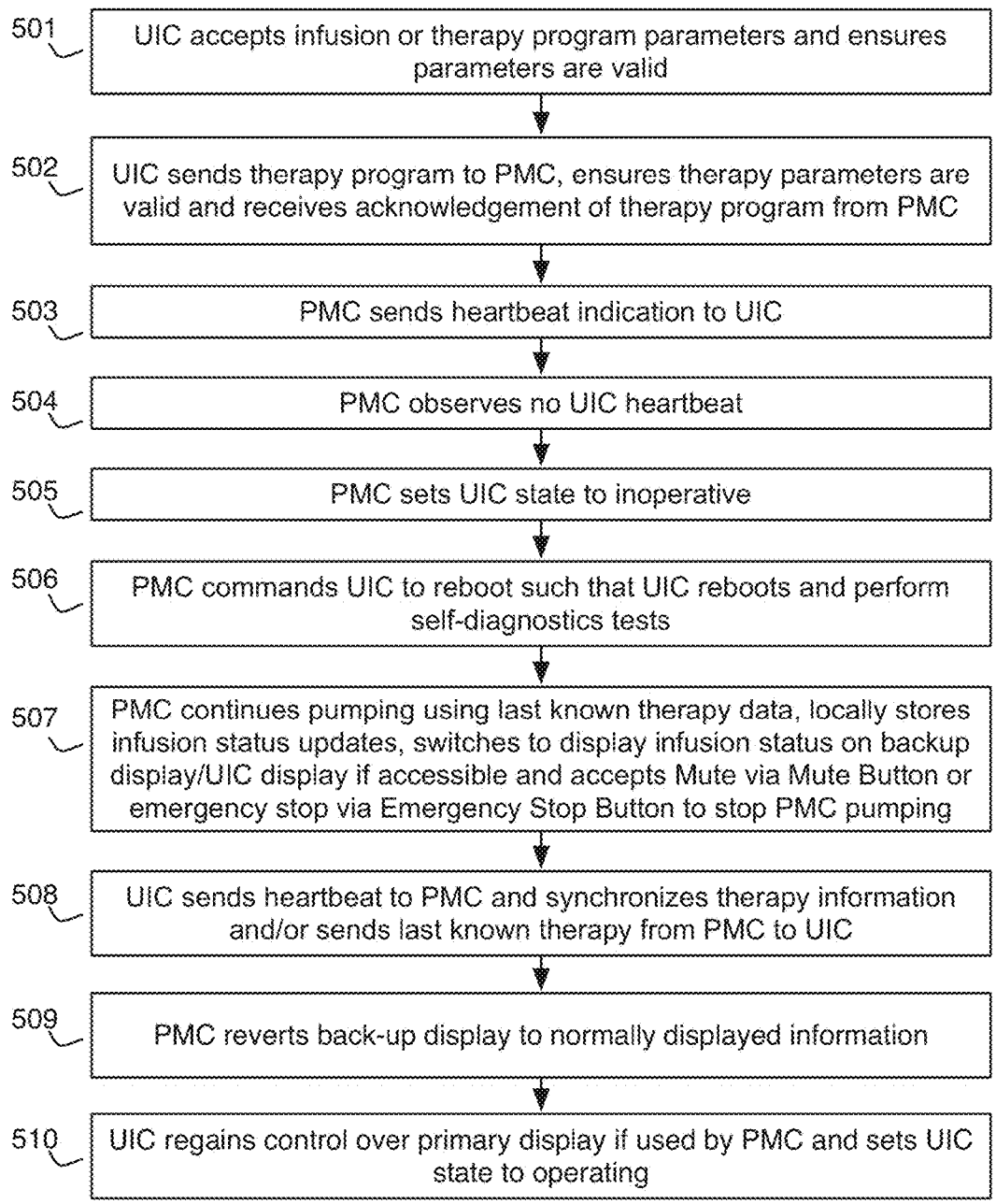
FIG. 5 shows a flowchart illustrating a response to the user interface controller malfunctioning during infusion, according to one or more embodiments of the invention.

FIG. 5 shows a flowchart illustrating a response due to a user interface controller malfunction during infusion, according to one or more embodiments of the invention. As shown in FIG. 5, at step 501, the UIC 102 may accept infusion or therapy parameters manually from a user or electronically from another computer system within a hospital (not shown), and ensure the parameters are valid. In at least one embodiment, at 502 the UIC 102 may send a therapy program to the PMC 101 and receive acknowledgement of the therapy program from the PMC 101. The PMC may send a heartbeat indication to the UIC 102 at 503. In one or more embodiments of the invention, the PMC 101 may not receive or otherwise observe a UIC 102 heartbeat at 504. The PMC may then set a UIC state to inoperative at 505, wherein pumping generally continues while the UIC 102 is inoperative. At 506, the PMC 101 may command the UIC 102 to reboot, or the UIC 102 may auto-reboot wherein in any case the UIC 102 reboots and performs self-diagnostic tests. The self-diagnostic tests may include T0 tests (power-on self-tests), T1 tests (tests prior to therapy start), and T2 tests (infusion active run-time self-diagnostic tests) or any other type of tests. At step 507, the PMC 101 may continue pumping using last known therapy data, locally store infusion status updates, display infusion status for example on backup display 203 or if available on the UIC display 202, as opposed to normal display of information as occurs when the UIC is operational. For example, infusion related status may be displayed albeit on a limited PMC text or graphics based display instead of normal air trap volume, downstream occlusion pressure, or other PMC typical information display. The system may accept a mute input via mute button 200, and/or an emergency stop signal from a user using the emergency stop button 201 in order to stop the PMC 101 from pumping. By way of one or more embodiments, when the emergency stop button 201 is used, the emergency stop signal is simultaneously sent to the UIC 102. In one or more embodiments, when the UIC 102 is inoperative, the touch display 202 may not be available to use a stop option on the touch display 202. In at least one embodiment, at step 508, the UIC 102 may then deliver a heartbeat indication to the PMC 101, and the PMC 101 may send a last known therapy to the UIC 102. In one or more embodiments, the PMC 101 may revert the back-up user interface 203 display to normally displayed information at step 509, and at 510, the UIC 102 may regain control over primary touch display 202 and the PMC 101 may set the UIC state to operating.

In one or more embodiments of the invention, if an error is detected during a T0 test, the system 100 may declare a system malfunction. In one or more embodiments, if an error is detected during a T1 test and the UIC 102 fails, the user may switch infusion channels or communication links or any combination thereof, perform a T1 self-diagnostics test and loop in one embodiment a maximum of three times before declaring a system malfunction. If an error is detected during a T1 test and the PMC 101 declares any malfunction or error, the PMC 101 may attempt to reboot, perform a PMC T0 self-diagnostic test, and if the PMC 101 continues to declare a malfunction or error, then the PMC 101 may declare a system malfunction. In one or more embodiments, optionally, if a dual or multi-channel configuration is used, and the second channel is not in use or inactive, the UIC 102 may move the therapy program to the unused (second) channel and declare that the current (first) channel is inoperative and requires service. During a T1 self-diagnostics test, the UIC 102 cannot declare an error or malfunction since the UIC 102 is not actively involved in therapy.

In one or more embodiments of the invention, if an error is detected during a T2 test and the UIC 102 declares a malfunction or error, each active PMC 101 may activate silence-able backup alarm tone using a mute button, switch backup screen to infusion status view, continue executing the full therapy program, and if the UIC 102 attempts to resynchronize, the PMC 101 may clear backup alarm tone if not muted using mute button, switch backup screen to normal view, such as displaying upstream occlusion pressure, downstream occlusion pressure, upstream air cumulative, downstream air cumulative, upstream air bubble and downstream air bubble, update UIC 102 with current status, such as infusion status and backlog of messages, and the PMC 101 may continue executing the full therapy program. In one or more embodiments of the invention, if an error is detected during a T2 test and the UIC 102 declares a malfunction or error, the UIC 102 may attempt a UIC reboot and perform a T0 self-diagnostics test. In at least one embodiment, if the UIC 102 passes the T0 self-diagnostics test, the UIC 102 may synchronize with the PMC 101, or several PMCs. If the UIC 102 fails the T0 self-diagnostics test, the UIC 102 may declare itself inoperative and state wherein service is required. In one or more embodiments of the invention, if an error is detected during a T2 test and the PMC 101 declares a malfunction or error, the PMC 101 may attempt to reboot itself, perform a T0 self-diagnostics, and if the PMC 101 continues to declare a malfunction or error, then the PMC 101 may declare a system malfunction. In one or more embodiments, optionally, if a dual or multiple channel configuration is used, and the second channel is not in use or inactive, the UIC 102 may move the therapy program to the unused (second) channel and declare that the current (first) channel is inoperative and requires service. In at least one embodiment, if the PMC 101 passes the T0 self-diagnostics test, the UIC 102 may synchronize with the PMC 101 to reprogram the PMC 101 with a current infusion status.

FIG. 6 shows exemplary pump motor controller associated displays under normal operation in the topmost screen. The figure also shows exemplary embodiments of displays under UIC failure wherein the PMC processor, e.g., second processor, is further configured to display a limited version of infusion information on the optional secondary user interface display that is normally displayed by said first processor on the first user interface display. As shown, under normal operation the second user interface display associated with the PMC displays downstream pressure and for example an Air Trap graphical display. Any other information displayed by any PMC is in keeping with the scope of the invention. Under UIC failure as shown in the middle PMC display, the display is switched to a limited version of the UIC display to shown any drugs, infusion programs, and/or other parameters. For example the secondary user interface display may show the battery voltage, e.g., as shown in the right middle screen as a standard battery icon. Any UIC reboot progress may also be displayed. If the UIC fails to reboot, the lower screen may be displayed, which shows the reboot to be unsuccessful and may also display the amount of time that the PMC may operate before infusion ceases.

In addition, one or more embodiments of the invention may include a new drug library parameter, for example a drug library location parameter that enables the UIC and/or PMC to operate in a desired manner associated with the location in which the UIC and PMC are to operate. For example, embodiments may include a new parameter, e.g., "Ward", or "Location-Type" parameters for example, which enables different types of displays, different volume levels for alarms or any other settable parameter for the UIC and/or PMC. This enables General Ward located UIC and PMC's to operate with full volume for alarms while enabling Pediatric Ward located UIC and PMC's to operate with quiet volume alarms so as not to disturb sleeping children. ICU Ward located UIC and PMC's may include other thresholds or alarms for operation that are more sensitive or conservative for example. Any other parameter associated with the UIC and/or PMC may be indexed or otherwise altered by storing an array of parameter values associated with different locations or wards for example. Any other type of data structure that enables UIC and/or PMC settings, for example two or more settings or drug library parameters to be altered by altering the Ward or Location-Type parameter is in keeping with the scope of the invention. In addition, for UIC failure scenarios, this setting enables the PMC to take on the location specific features for alarms in the case of UIC failure, wherein the PMC takes on the responsibility of showing at least a portion of data that the UIC normally shows when operational.

While the invention herein disclosed has been described by means of specific embodiments and applications thereof, numerous modifications and variations could be made thereto by those skilled in the art without departing from the scope of the invention set forth in the claims.

What is claimed is:

1. A fail-safe drug infusion system comprising:
   a user interface controller comprising
     a first processor;
     a first memory coupled with said first processor;
     a user interface display coupled with said first processor;
   a pump motor controller comprising
     a second processor;
     a second memory coupled with said second processor;
     a secondary display coupled with said second processor;
     wherein said second processor is configured to control a pump motor to deliver a fluid;
   a communication link coupled with the user interface controller and the pump motor controller;
   wherein said first processor and said second processor are communicatively synchronized via said communication link;
   wherein each of said first memory of said first processor and said second memory of said second processor comprise redundant drug infusion delivery information;
   wherein said first processor is configured to send a first delivery request to said second processor;
   wherein when said second processor receives said first delivery request from said first processor, said second processor is configured to command said pump motor to deliver said fluid;
   wherein if said first processor fails or if said communication link between said first processor and said second processor is interrupted, said second processor is configured to continue to apply fail-safe therapy to command said pump motor to deliver said fluid;
   wherein said first processor is configured to send a first delivery suspend request to said second processor in order to suspend said first delivery request; and
   wherein said first processor is configured to send said first delivery suspend request when one or more of said first processor and said second processor detect an error.

2. The fail-safe drug infusion system of claim 1, wherein when said pump motor delivers said fluid, said second processor is configured to create a status report with status report information, such that said second processor is configured to send said status report information to said first processor.

3. The fail-safe drug infusion system of claim 2, wherein first processor is configured to receive said status report information from said second processor and update a fluid delivery status display on said user interface display, wherein said information comprises at least one of
said activated fluid deliveries and,
completed fluid deliveries.

4. The fail-safe drug infusion system of claim 1, wherein said first processor is configured to send said first delivery suspend request when a user initiates a first delivery suspend command.

5. The fail-safe drug infusion system of claim 1, wherein said second processor is configured to
receive said first delivery suspend request,
stop said pump motor delivery of said fluid prior to completion of said delivery of said fluid, such that undelivered fluid volume remains, and
suspend said first delivery request.

6. The fail-safe drug infusion system of claim 5, wherein said first processor is configured to send a second delivery request to said second processor
wherein when said second processor receives said second delivery request, said second processor is configured to command said pump motor to deliver fluid associated with said second delivery request.

7. The fail-safe drug infusion system of claim 6, wherein when said second delivery request fluid delivery is completed, said second processor updates said fluid delivery status display, and said first processor is configured to send said suspended first delivery request to said second processor such that said pump motor delivers said remaining undelivered fluid volume.

8. The fail-safe drug infusion system of claim 6, wherein if said communication link between said first processor and said second processor is interrupted during fluid delivery of said second delivery request, upon completion of said second delivery request, said second processor is configured to locate said suspended first delivery request and deliver said remaining undelivered fluid volume.

9. The fail-safe drug infusion system of claim 5, wherein when said remaining undelivered fluid volume is delivered, said first processor is configured to process a next delivery request, such that said pump motor delivers said fluid.

10. The fail-safe drug infusion system of claim 6, wherein when said remaining undelivered fluid volume is delivered, said second processor is configured to process a next delivery request, such that said pump motor delivers said fluid.

11. The fail-safe drug infusion system of claim 1, wherein when said communication link between said first processor and said second processor is interrupted, said pump motor controller is configured to provide one or more of a visual alarm and an audio alarm on said secondary display.

12. The fail-safe drug infusion system of claim 1, wherein the secondary display is a secondary user interface display and if said first processor fails or if said communication link between said first processor and said second processor is interrupted, said second processor is further configured to display a limited version of infusion information on said secondary user interface display that is normally displayed by said first processor.

13. The fail-safe drug infusion system of claim 1, wherein said first processor or second processor or both include a drug library location parameter that enables the user interface controller (UIC), pump motor controller (PMC) or both to operate in a desired manner associated with the location in which the UIC and PMC are to operate.

14. A fail-safe drug infusion system comprising:
a user interface controller comprising
a first processor;
a first memory coupled with said first processor;
a user interface display coupled with said first processor;
a pump motor controller comprising
a second processor;
a second memory coupled with said second processor;
a secondary display coupled with said second processor;
wherein said second processor is configured to control a pump motor to deliver a fluid;
a communication link coupled with the user interface controller and the pump motor controller;
wherein said first processor and said second processor are communicatively synchronized via said communication link;
wherein each of said first memory of said first processor and said second memory of said second processor comprise redundant drug infusion delivery information;
wherein said first processor is configured to send a first delivery request to said second processor;
wherein when said second processor receives said first delivery request from said first processor, said second processor is configured to command said pump motor to deliver said fluid;
wherein if said first processor fails or if said communication link between said first processor and said second processor is interrupted, said second processor is configured to continue to apply fail-safe therapy to command said pump motor to deliver said fluid; and
wherein if said communication link between said first processor and said second processor is reestablished, said second processor is configured to enter a recovery synchronization mode, such that said second processor is configured to send status report information to said first processor, wherein said status report information comprises updated fluid delivery status.

15. A fail-safe drug infusion system comprising:
a user interface controller comprising
a first processor;
a first memory coupled with said first processor;
a user interface display coupled with said first processor;
a pump motor controller comprising
a second processor;
a second memory coupled with said second processor;
a secondary display coupled with said second processor;
wherein said second processor is configured to control a pump motor to deliver a fluid;
a communication link coupled with the user interface controller and the pump motor controller;
wherein said first processor and said second processor are communicatively synchronized via said communication link;
wherein each of said first memory of said first processor and said second memory of said second processor comprise redundant drug infusion delivery information;
wherein said first processor is configured to send a first delivery request to said second processor;

wherein when said second processor receives said first delivery request from said first processor, said second processor is configured to command said pump motor to deliver said fluid;

wherein if said first processor fails or if said communication link between said first processor and said second processor is interrupted, said second processor is configured to continue to apply fail-safe therapy to command said pump motor to deliver said fluid; and wherein when said communication link between said first processor and said second processor is interrupted, said second processor is configured to:
provide therapy for a predefined time, remaining battery life, or fluid delivery volume; and
display information on said secondary display, wherein said information comprises updated fluid delivery status.

16. A fail-safe drug infusion system comprising:
a user interface controller comprising
a first processor;
a first memory coupled with said first processor;
a user interface display coupled with said first processor;
a pump motor controller comprising
a second processor;
a second memory coupled with said second processor;
a secondary display coupled with said second processor;
wherein said second processor is configured to control a pump motor to deliver a fluid;
a communication link coupled with the user interface controller and the pump motor controller;
wherein said first processor and said second processor are communicatively synchronized via said communication link;
wherein each of said first memory of said first processor and said second memory of said second processor comprise redundant drug infusion delivery information;
wherein said first processor is configured to send a first delivery request to said second processor;
wherein when said second processor receives said first delivery request from said first processor, said second processor is configured to command said pump motor to deliver said fluid;
wherein if said first processor fails or if said communication link between said first processor and said second processor is interrupted, said second processor is configured to continue to apply fail-safe therapy to command said pump motor to deliver said fluid; and
wherein when said communication link between said first processor and said second processor is interrupted, said second processor is configured to display a duration of how long said second processor is able to operate independently of said first processor on said secondary display.

17. A fail-safe drug infusion system comprising:
a user interface controller comprising
a first processor;
a first memory coupled with said first processor;
a user interface display coupled with said first processor;
a pump motor controller comprising
a second processor;
a second memory coupled with said second processor;
a secondary user interface display coupled with said second processor;
wherein said second processor is configured to control a pump motor to deliver a fluid;
a communication link coupled with the user interface controller and the pump motor controller;
wherein said first processor and said second processor are communicatively synchronized via said communication link;
wherein each of said first memory of said first processor and said second memory of said second processor comprise redundant drug infusion delivery information;
wherein said first processor is configured to send a first delivery request to said second processor;
wherein when said second processor receives said first delivery request from said first processor, said second processor is configured to command said pump motor to deliver said fluid;
wherein if said first processor fails or if said communication link between said first processor and said second processor is interrupted, said second processor is configured to
continue to apply fail-safe therapy to command said pump motor to deliver said fluid and
display information from said second processor that includes infusion information that is normally displayed by said first processor and
display a duration of how long said second processor is able to operate independently of said first processor on said secondary user interface display; and,
wherein if said communication link between said first processor and said second processor is reestablished, said second processor is configured to enter a recovery synchronization mode, such that said second processor is configured to send status report information to said first processor, wherein said status report information comprises updated fluid delivery status.

* * * * *

UNITED STATES PATENT AND TRADEMARK OFFICE
CERTIFICATE OF CORRECTION

PATENT NO.        : 9,662,436 B2
APPLICATION NO.   : 14/490450
DATED             : May 30, 2017
INVENTOR(S)       : Anatoly S. Belkin It is certified that error appears in the above-identified patent and that said Letters Patent is hereby corrected as shown below:

In Column 2 (page 2, item (56)) at Line 43, Under Other Publications, change "Anaethesia," to --Anesthesia,--.

Sheet 1 of 6 (Referral Numeral 114, Figure 1) at Line 1, Change "Dlsplay" to --Display--.

Signed and Sealed this
Fourteenth Day of November, 2017

Joseph Matal
*Performing the Functions and Duties of the
Under Secretary of Commerce for Intellectual Property and
Director of the United States Patent and Trademark Office*